United States Patent
Sheldon et al.

(10) Patent No.: US 6,259,587 B1
(45) Date of Patent: Jul. 10, 2001

(54) DIRECT CURRENT MOTOR SAFETY CIRCUITS FOR FLUID DELIVERY SYSTEMS

(75) Inventors: Moberg Sheldon, Granada Hills; James D. Causey, Simi Valley; Herman Lee Renger, Calabasas, all of CA (US)

(73) Assignee: MiniMed Inc., Northridge, CA (US)

( * ) Notice: Subject to any disclaimer, the term of this patent is extended or adjusted under 35 U.S.C. 154(b) by 0 days.

(21) Appl. No.: 09/335,008

(22) Filed: Jun. 17, 1999

(51) Int. Cl.$^7$ .................................................. H02H 5/04
(52) U.S. Cl. ............................. 361/23; 361/33; 318/434; 323/276
(58) Field of Search .................... 361/23, 33, 31, 361/86, 88; 318/434; 388/903; 323/265, 293, 276

(56) References Cited

U.S. PATENT DOCUMENTS

| | | | |
|---|---|---|---|
| 3,764,873 | 10/1973 | Elliott et al. | 318/252 |
| 3,931,557 | * 1/1976 | Osburn | 318/434 |
| 4,030,012 | 6/1977 | Buhler et al. | 318/565 |
| 4,207,503 | 6/1980 | Irschik et al. | 318/139 |
| 4,308,866 | 1/1982 | Jelliffe et al. | 128/214 E |
| 4,854,324 | 8/1989 | Hirschman et al. | 128/655 |
| 4,873,453 | * 10/1989 | Schmerda et al. | 307/130 |
| 4,980,624 | * 12/1990 | Bernhardt | 318/434 |
| 5,243,243 | * 9/1993 | Andrews | 310/72 |
| 5,414,792 | * 5/1995 | Shorey | 388/811 |
| 5,773,945 | * 6/1998 | Kim et al. | 318/434 |

FOREIGN PATENT DOCUMENTS

| | | |
|---|---|---|
| 0324614 | 7/1989 | (EP) . |
| 2223636 | 4/1990 | (GB) . |
| 9726703 | 7/1997 | (WO) . |

* cited by examiner

Primary Examiner—Michael J. Sherry
Assistant Examiner—Kim Huynh
(74) Attorney, Agent, or Firm—MiniMed Inc.

(57) ABSTRACT

A safety circuit system for a DC driven device for use with a fluid delivery system includes a first voltage potential DC power line, a second voltage potential DC power line, a controller and a safety circuit. The first voltage potential DC power line is coupled to provide a first voltage potential to the DC driven device, and the second voltage potential DC power line is coupled to provide a second voltage potential to the DC driven device such that the second voltage potential is different relative to the first potential. The controller controls at least the first voltage potential on the first voltage potential DC power line. The safety circuit has an enable state and a disable state, in which the default state is the disable state. The safety circuit is coupled to the controller, and the controller controls the safety circuit to place the safety circuit in the enable state independently of controlling the first voltage potential on the first voltage potential DC power line. The safety circuit is operatively coupled to at least one of the first and second voltage potential DC power lines to inhibit DC flow and operation of the DC driven device when the safety circuit is in the disable state and to permit DC flow and operation of the DC driven device when the safety circuit is in the enable state such that the operation of the DC driven device will occur when the safety circuit is in the enable state. In one version the DC driven device is a DC motor in an infusion pump, while in other versions the DC driven device is a gas generator in an infusion pump. Preferably, the safety circuit is controlled by an AC signal from the controller such that the safety circuit is enabled by the AC signal to permit DC flow and enable the forward motion of the DC motor while the AC signal is provided by the controller.

15 Claims, 8 Drawing Sheets

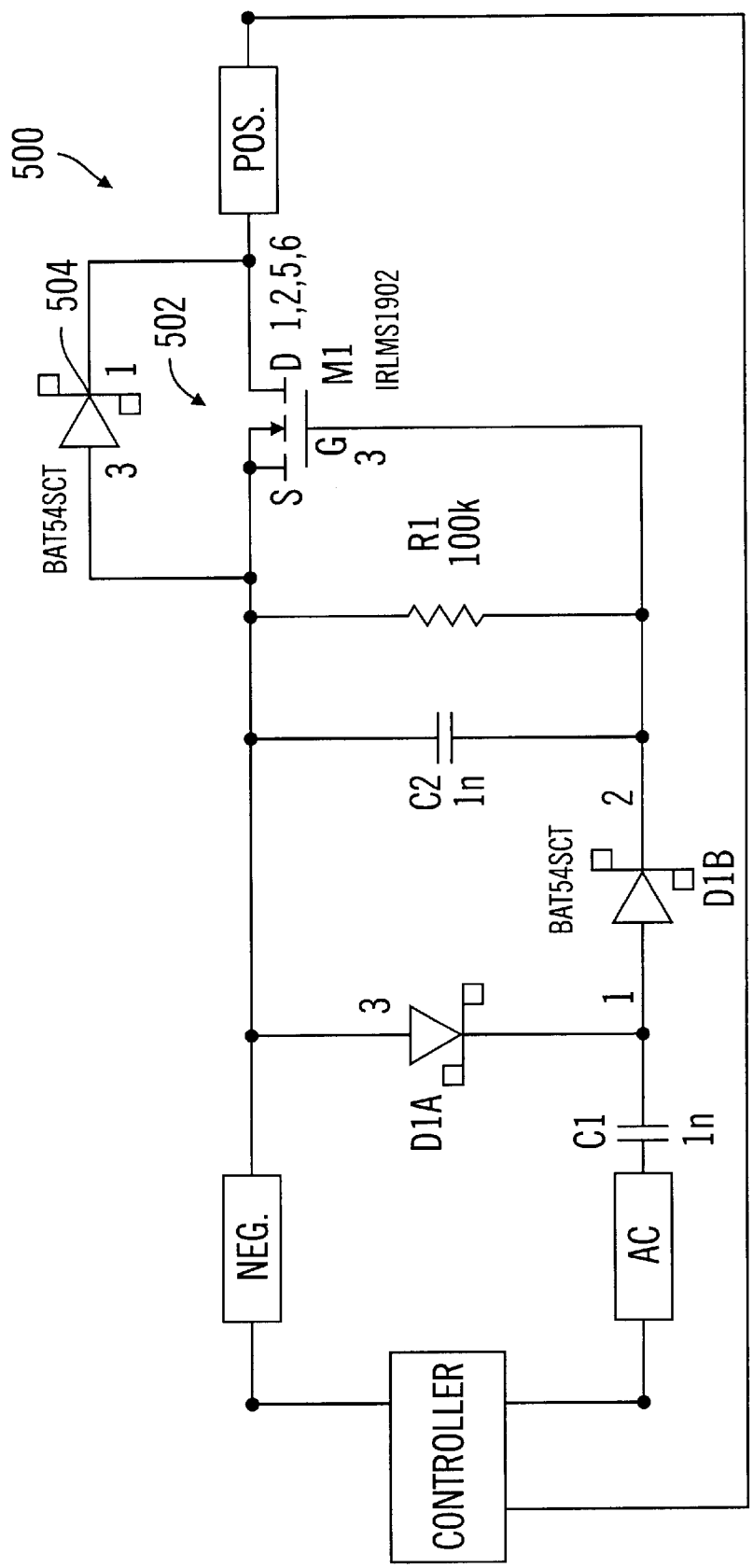
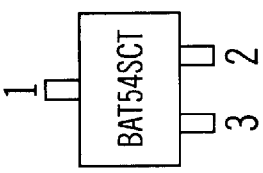
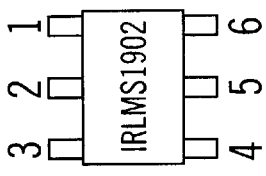
FIG. 5(a)
FIG. 5(b)
FIG. 5(c)

DIRECT CURRENT MOTOR SAFETY CIRCUITS FOR FLUID DELIVERY SYSTEMS

FIELD OF THE INVENTION

This invention relates to direct current (DC) motor safety circuits in fluid delivery systems and, in particular embodiments, to safety circuits for DC motors in medication/drug infusion pumps to inhibit accidental over delivery of medications/drugs due to DC motor control circuit failures.

BACKGROUND OF THE INVENTION

Conventional drug delivery systems such as infusion pumps that deliver insulin over a period of time utilize a variety of motor technologies to drive an infusion pump. Typical motor technologies include direct current (DC) motors, stepper motors, or solenoid motors. Each motor type has various advantages and disadvantages related to cost, reliability, performance, weight, and safety.

In drug delivery using infusion pumps, the accuracy of medication delivery is critical (such as for insulin, HIV drugs or the like), since minor differences in medication quantity can dramatically affect the health of the patient. Thus, safeguards must be designed into the delivery system to protect the patient from over or under delivery of medication. For example, in the case where insulin is administered via an infusion pump to a diabetic patient, excessive drug delivery could cause complications due to hypoglycemia, and could possibly even result in death. Therefore, controlled delivery with safeguards against over delivery of medications is required for drug delivery systems when over delivery could result in complications, permanent damage, or death of the patient.

In conventional systems, these safeguards against over delivery have been incorporated into the drive systems of infusion pumps in varying ways. For example, the motor control electronics utilize cross checks, encoder counts, motor current consumption, occlusion detection, or the like, as a form of feedback to guard against over or under delivery of medication. However, one drawback to this approach can occur if the control electronics in a DC motor driven infusion pump were to fail, such that a direct short occurs from the power source to a DC motor in the infusion pump. For example, in one failure mode, it would be possible for the DC motor to drive continuously for an excessive period of time, for example, until the power source was depleted or removed, or until the short was removed. This condition is commonly referred to as motor "run away", and could result in all of the medication contained in the infusion pump being infused immediately over too short a period of time resulting in injury or death to the patient.

To avoid this drawback, some infusion pump manufactures have avoided the use of DC motors and have instead utilized solenoid or stepper motor technologies. With these motor types, any short in the control electronics, would only result in, at most, a single motor step. Therefore, motor "run away" would not occur. Thus, this avoids the problem of a "run away" failure. However, a drawback to the use of solenoid or stepper motor technologies is they generally have a less efficient performance and tend to cost more as compared to the DC motors.

SUMMARY OF THE DISCLOSURE

It is an object of an embodiment of the present invention to provide improved DC motor safety circuits, which obviate for practical purposes, the above mentioned limitations.

According to an embodiment of the invention, a safety circuit system for a DC driven device for use with a fluid delivery system includes a first voltage potential DC power line, a second voltage potential DC power line, a controller and a safety circuit. The first voltage potential DC power line is coupled to provide a first voltage potential to the DC driven device, and the second voltage potential DC power line is coupled to provide a second voltage potential to the DC driven device such that the second voltage potential is different relative to the first potential. The controller controls at least the first voltage potential on the first voltage potential DC power line. The safety circuit has an enable state and a disable state, in which the default state is the disable state. The safety circuit is coupled to the controller, and the controller controls the safety circuit to place the safety circuit in the enable state independently of controlling the first voltage potential on the first voltage potential DC power line. The safety circuit is operatively coupled to at least one of the first and second voltage potential DC power lines to inhibit DC flow and operation of the DC driven device when the safety circuit is in the disable state and to permit DC flow and operation of the DC driven device when the safety circuit is in the enable state such that the operation of the DC driven device will occur when the safety circuit is in the enable state. In preferred embodiments, the DC driven device is a DC motor in an infusion pump. Alternatively, the DC driven device is a gas generator in an infusion pump. In preferred embodiments, the safety circuit is controlled by an AC signal from the controller such that the safety circuit is enabled by the AC signal to permit DC flow and enable the forward motion of the DC motor while the AC signal is provided by the controller.

In embodiments that utilize a DC motor, the safety circuit being in the disable state operates to inhibit the forward motion of the DC motor when the difference of the first voltage potential relative to second voltage potential is positive. In addition, the safety circuit being in the disable state is inoperative to inhibit a reverse motion of the DC motor when the difference of the first voltage potential relative to second voltage potential is negative. Alternatively, or in addition to, the safety circuit being in the disable state operates to inhibit a reverse motion of the DC motor when the difference of the first voltage potential relative to second voltage potential is negative. In addition, the safety circuit being in the disable state operates to inhibit the forward motion of the DC motor when the difference of the first voltage potential relative to second voltage potential is negative. Further, the safety circuit being in the disable state is inoperative to inhibit a reverse motion of the DC motor when the difference of the first voltage potential relative to second voltage potential is positive. Alternatively, the safety circuit being in the disable state operates to inhibit a reverse motion of the DC motor when the difference of the first voltage potential relative to second voltage potential is positive.

Preferred embodiments are directed to an infusion pump, in which the safety circuit is used to prevent operation of the DC motor during a controller failure to prevent accidental delivery of excess fluid. In particular embodiments, the safety circuit is integral with the DC motor. In other embodiments, the safety circuit is co-located with the controller.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 5(a) is a schematic diagram of a safety circuit that is a further variation of the embodiment shown in FIG. 3.

FIG. 5(b) is a top view of a pin out diagram for a component used in the circuit shown in FIG. 5(a).

FIG. 5(c) is a top view of a pin out diagram for another component used in the circuit shown in FIG. 5(a).

DETAILED DESCRIPTION OF THE PREFERRED EMBODIMENTS

Figure 1:
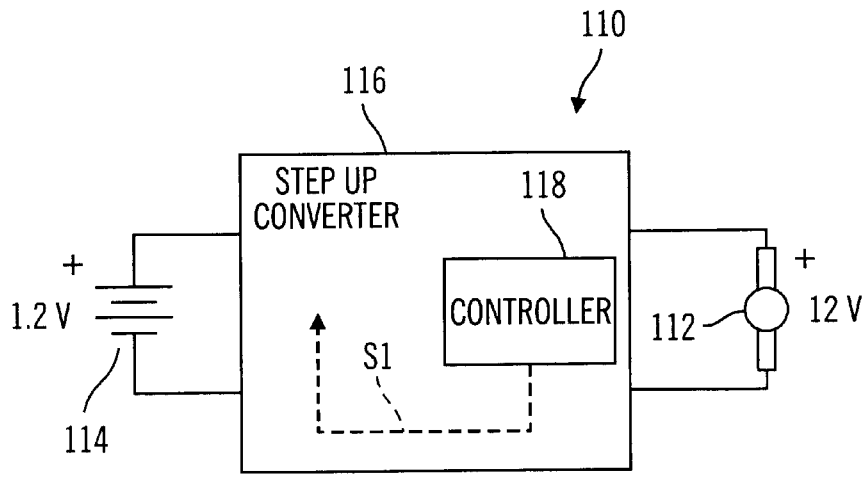
FIG. 1 is a schematic diagram of a safety circuit in accordance with a first embodiment of the present invention.

As shown in the drawings for purposes of illustration, the invention is embodied in safety circuits for direct current (DC) motors used in fluid delivery systems. In preferred embodiments of the present invention, controllers that provide a signal to the safety circuit, in addition to providing power for the DC motor in an infusion pump, that enables the DC motor to operate only when an enabling signal is provided to the safety circuit. However, it will be recognized that further embodiments of the invention may be used to inhibit motor operation with additional signals or by controlling other aspects of the infusion pump. The safety circuits are primarily adapted for use in infusion pumps that deliver medication (or fluid) to subcutaneous human tissue. However, still further embodiments may be used with infusion pumps for other types of tissue, such as muscle, lymph, organ tissue, veins, arteries or the like, and used in animal tissue. The infusion pumps are also primarily for external use; however, alternative embodiments may be implanted in the body of a patient. The fluid delivery systems are also primarily for delivery of medication, drugs and/or fluids to a patient; however other embodiments may be used with other fluid delivery systems that require a high degree of confidence that a DC motor "run away" will not occur, such as in certain manufacturing techniques or the like. Preferred embodiments are directed to safety circuits for DC motors. However, alternative embodiments may be used with other DC driven devices, such as a DC activated gas generator in an infusion pump or the like.

Preferred embodiments are directed to circuits and methods for using DC motor technology in fluid delivery systems with additional safety circuits to prevent DC motor "run away". Use of this technology obviates the need for the use of comparatively less efficient and more expensive stepper motor and solenoid motors. All of the illustrated embodiments include a DC motor and some DC motor control electronics, although other components or DC driven devices may be used. The control electronics may be relatively simple, such as only including the capability of turning the DC motor on and off by supplying power for the duration of a key press, or may be more complex using microprocessors having multiple programmable control profiles utilizing feedback from an encoder, driving current or the like.

FIG. 1 illustrates a safety circuit 110 in accordance with a first embodiment of the present invention. In this embodiment, a DC motor 112 is configured to have a nominal voltage winding that is significantly higher then a supply voltage from a battery 114. To generate a sufficient voltage to operate the DC motor 112, the safety circuit 110 utilizes a DC-DC step up converter 116 (or similar), that includes an integral controller 118, between the battery 114 and the DC motor 112 to drive the DC motor 112 at its rated voltage (see FIG. 1). Generally, when a DC motor is supplied with the rated voltage (and also assuming there is sufficient current available), the DC motor will provide a known torque . If, for example, the supply voltage is halved, then the DC motor will only provide approximately half the full voltage output torque. However, a two, or more, times DC-DC step up converter could be utilized between the battery and the DC motor to provide the rated voltage to the DC motor. Thus, to provide a safety circuit, the nominal motor voltage winding is selected to be some large multiple of the supply voltage from the battery, such as ten times, or the like, higher then the supply voltage from the battery. Therefore, if the battery 114 is shorted directly to the DC motor 112 (i.e., as when there is an control electronics 118 failure and/or DC-DC step up converter 116), the DC motor's 112 output torque would only be approximately ⅒ of the rated value.

Generally, if the friction in the complete drive system (e.g., drive gears, shaft, or the like) is approximately ⅒ of the nominal rated value, the DC motor 112 will not have enough available torque to drive the system and cause a "run away" condition. To drive the DC motor 112 with sufficient torque, a DC-DC step up converter 116 would be required with approximately a ten times step up capability. For additional safety, alternative embodiments of the safety circuit 10 would include the DC-DC step up converter 116 such that it would only be enabled by an additional internal signal S1 (shown in dashed lines) from the integral control electronics 118. Thus, if the control electronics 118 were to fail, there would be no enable signal to provide the required step up voltage to drive the DC motor 12 in a "run away" condition. Alternative embodiments may utilize different battery supply voltages to rated nominal motor voltages ratios, with the choice being based on system friction, tolerance for movement, cost of control electronics and DC motors, or the like. In further alternatives, the control electronics 118 may be separated from the DC-DC step up converter 116 and provided as a discrete element that is placed before or after the DC-DC step up converter 116.

Figure 2:
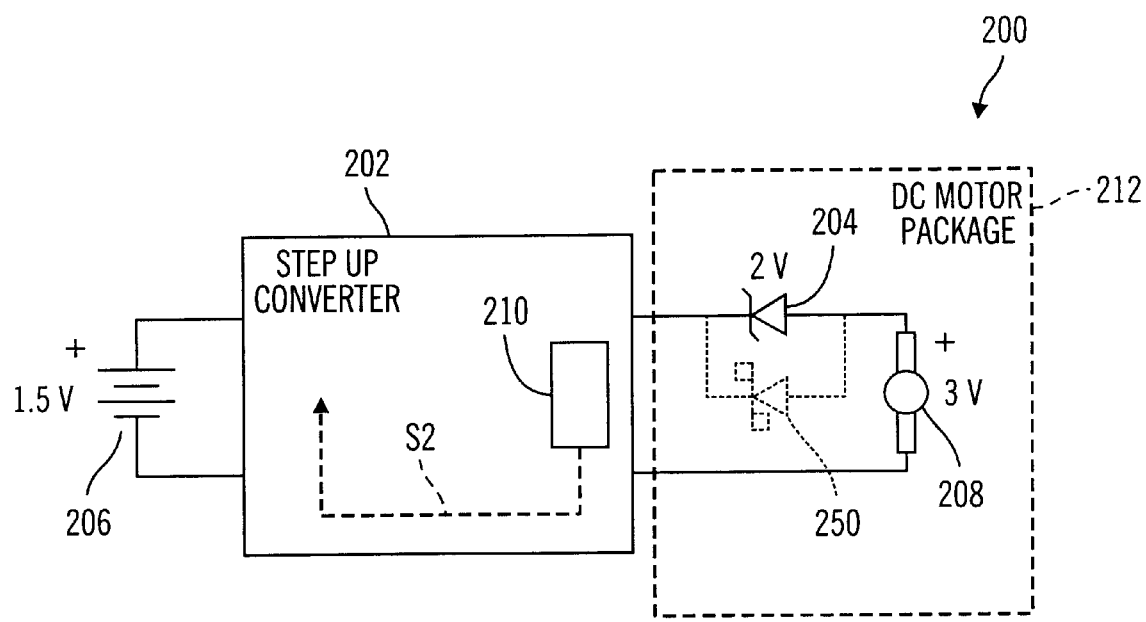
FIG. 2 is an illustrative schematic diagram of a safety circuit in accordance with a second embodiment of the present invention.

FIG. 2 illustrates a safety circuit 200 in accordance with a second embodiment of the present invention that builds upon the embodiment shown in FIG. 1. The safety circuit 200 utilizes a DC-DC step up converter 202 (that includes integral control electronics 210) and a Zener diode 204. The DC-DC step up converter 202 converts the supply voltage from the battery 206 to a value corresponding to the sum of the rated motor winding voltage of the DC motor 208 and the Zener diode 204. For instance, if the DC motor 208 has 3.0 volt motor winding and the Zener diode 204 has a breakdown voltage of 2.0 volts, the DC-DC step up converter 202 must provide 5.0 volts to facilitate operation of the DC motor 208 at its nominal rated voltage, if it is desired to drive the DC motor 208 at the rated voltage. Thus, in this example, when the supply voltage from the battery 206 is stepped up to 5 volts as a positive voltage potential, 2 volts are lost through the Zener diode 204 and 3 volts are provided for operation of the DC motor 208. In the reverse direction (i.e. a negative voltage potential), the DC-DC step up converter 202 only needs to step up the 1.5 volts supply voltage from the battery 206 to 3 volts, since there is little loss through the Zener diode 204 in the reverse direction. In an alternative embodiment, a Schottky diode 250 (shown in dashed lines in FIG. 2) may be placed in parallel with the Zener diode 204 to insure a low and predictable voltage drop in the reverse direction (i.e., negative voltage potential). Alternatively, if a higher speed rewind (e.g., more torque) is desired and/or required, the DC-DC step up converter 202 can still be stepped up to the 5 volts to over drive the 3 volt rated DC motor 208. Alternatively, the DC-DC step up converter 202 can provide a range of various voltage values to drive the DC motor 208 at different ratings in either the forward or the reverse directions.

In this embodiment, if the integral control electronics 210 failed and caused a direct short between the battery 206 and the DC motor 208 with the reversed biased Zener diode 202 (or a reversed biased Zener diode 202 in parallel with a Schottky diode 250), the DC motor 208 would not operate in the forward direction (i.e., there would be no drug delivery), and would have only a fraction of the rated torque in the rewind direction (or no rewinding if sufficient friction is present in the drive mechanism). For additional safety, alternative embodiments of the safety circuit 200 would include the DC-DC step up converter 202 such that it would only be enabled by an additional internal signal S2 (shown in dashed lines) from the control electronics 210. Thus, if the control electronics 210 were to fail, there would be no enable signal to provide the required step up voltage to drive the DC motor 208 in a "run away" condition. In preferred embodiments, the Zener diode 204 is contained within the DC motor package 212 (see also FIG. 7) so that the DC motor 208 is protected independently of the type of control electronics 210 to which the DC motor 208 is connected. In alternative embodiments, the Zener diode 204 could be contained within the control electronics and the electronics are then connected to a conventional DC motor (see also FIG. 8). In alternative embodiments, a second Zener may be used, which is reversed with respect to the first diode and in series with the first diode such that the DC motor operates similarly in both directions. In the event of direct short to the DC motor in the reverse direction, the battery voltage would not be enough to run the motor 208 in either direction. In further alternatives, the control electronics 210 may be separated from the DC-DC step up converter 202 and provided as a discrete element that is placed before or after the DC-DC step up converter 202.

In the first two embodiments, "run away" of the DC motor is substantially prevented However, if the system were to fail such that a short were maintained between the stepped up voltage from the DC-DC converter to the DC motor and/or the Zener diode failed, then the potential for motor "run away" exists with the above embodiments.

Figure 3:
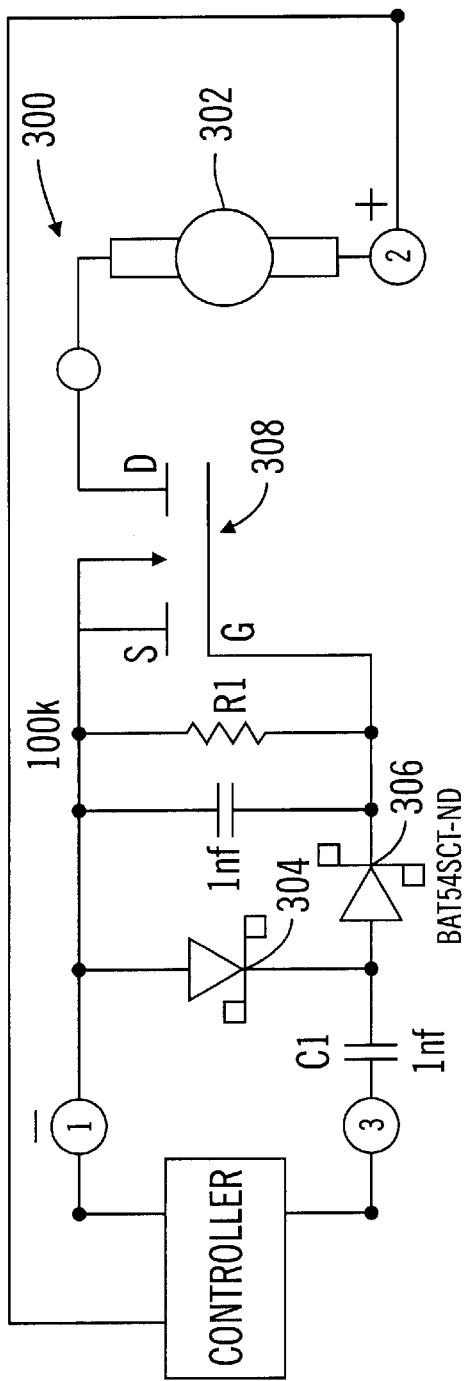
FIG. 3 is a schematic diagram of a safety circuit in accordance with a third embodiment of the present invention.
Figure 8:
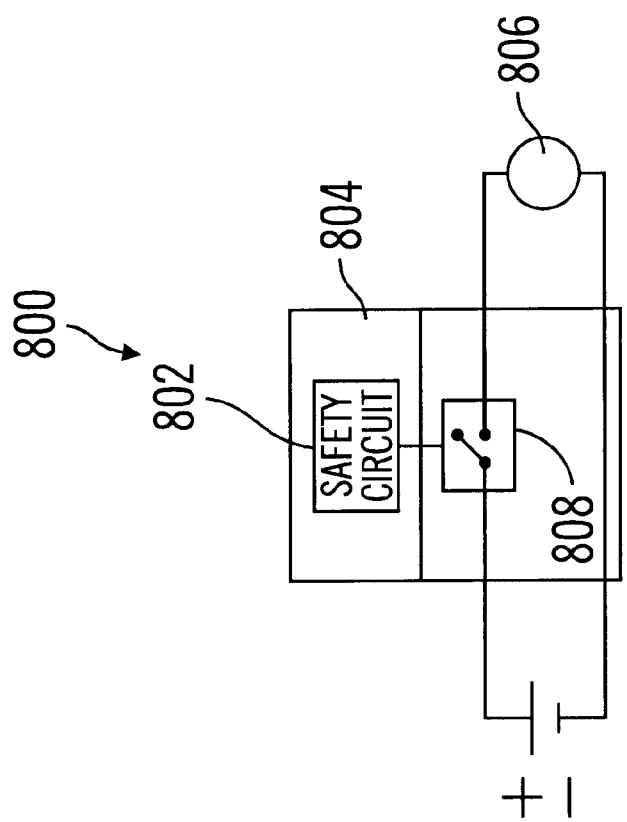
FIG. 8 is a simplified schematic of a motor and safety circuit in accordance with an alternative embodiment of the present invention.
Figure 7:
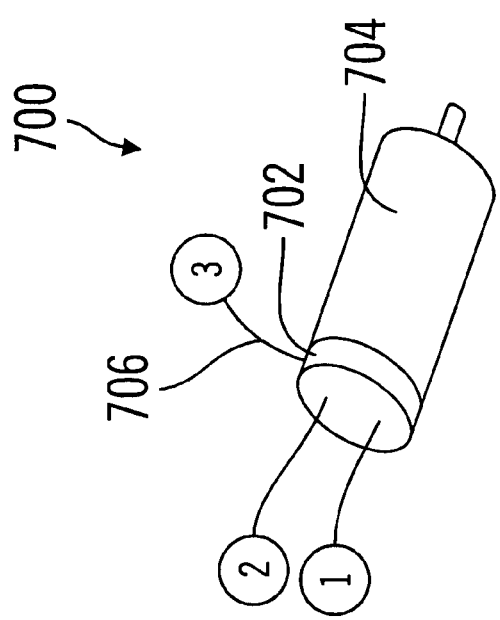
FIG. 7 is a perspective view of a motor in accordance with an embodiment of the present invention.

FIG. 3 illustrates a safety circuit 300 in accordance with a third embodiment of the present invention, which includes further enhancements to provide protection against DC motor 302 "run away". The safety circuit 300 includes additional electronics added to the DC motor package (as shown in FIG. 7) that are independent of the control electronics. Alternatively, the additional electronics may be included in the control electronics (as shown in FIG. 8) or as a separate set of control electronics (not shown). In preferred embodiments, the control electronics must provide a specific signal (at terminal 3) to the additional electronics to allow the DC motor 302 to operate. As shown in FIG. 3, the rated supply voltage from the battery (not shown) is supplied to terminals 1 and 2 as a negative and positive voltage potential, respectively, to control operation of the DC motor 302 in the forward direction. However, current will not pass through the DC motor 302 until a specific AC signal (e.g., a 3 volt Peak-to-Peak Square wave at approximately 32 kHz—see FIGS. 9–11) is provided to terminal 3 and the safety circuit 300 by the control electronics. This provides a second independent system to control the operation of the DC motor 302. For a "run away" to occur the control electronics must short the battery to the power terminals 1 and 2, and must also provide an AC signal to terminal 3 of the safety circuit 300. Thus, if a direct short does occur between the battery and the power terminals 1 and 2 with the safety circuit 300, the DC motor 302 will not operate, since the required AC signal at terminal 3 is not present. Preferably, the safety circuit 300 uses two Schottky diodes 304 and 306 (e.g., BAT54SCT-ND from Zetex) and a FET 308 ((e.g., IRMLMS 1902 from International Rectifier).

In operation, when the control electronics provide a positive DC voltage potential at terminal 2, and a negative voltage potential at terminal 1, the DC motor 302 will not operate since the gate G of the FET 308 does not have a positive signal applied to it derived from the input at terminal 3 of the safety circuit 300. In this situation, the gate G blocks the flow of current from the drain D to the source S of the FET 308. DC flow through terminal 3 is blocked by the capacitor C1. Thus, the DC motor 302 will not operate, if there is no AC signal applied to terminal 3 of the safety circuit 300.

Figure 9:
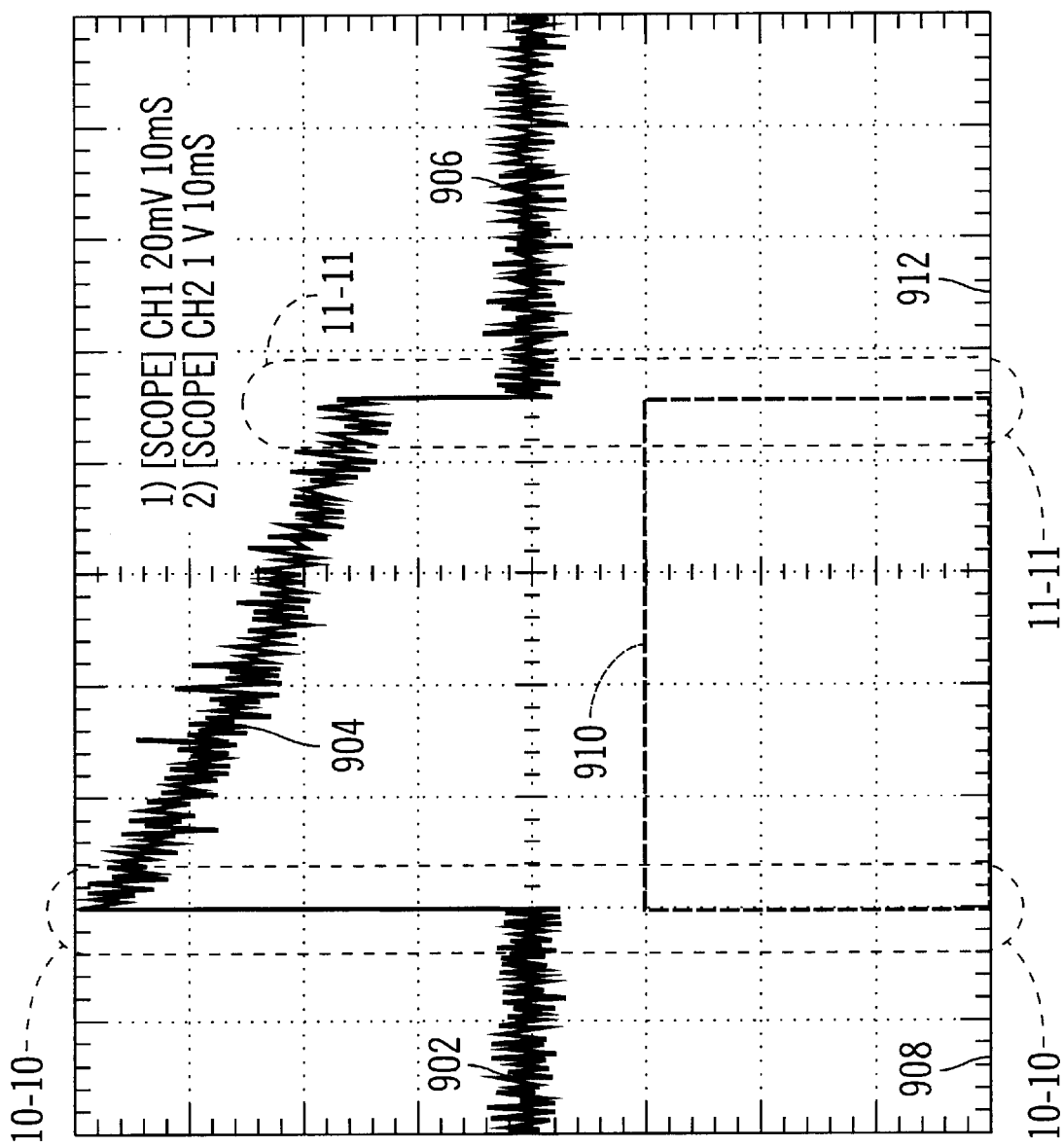
FIG. 9 is a waveform diagram illustrating operation of the safety circuit and power supplied to a DC motor in accordance with the embodiments of the present invention.
Figure 10:
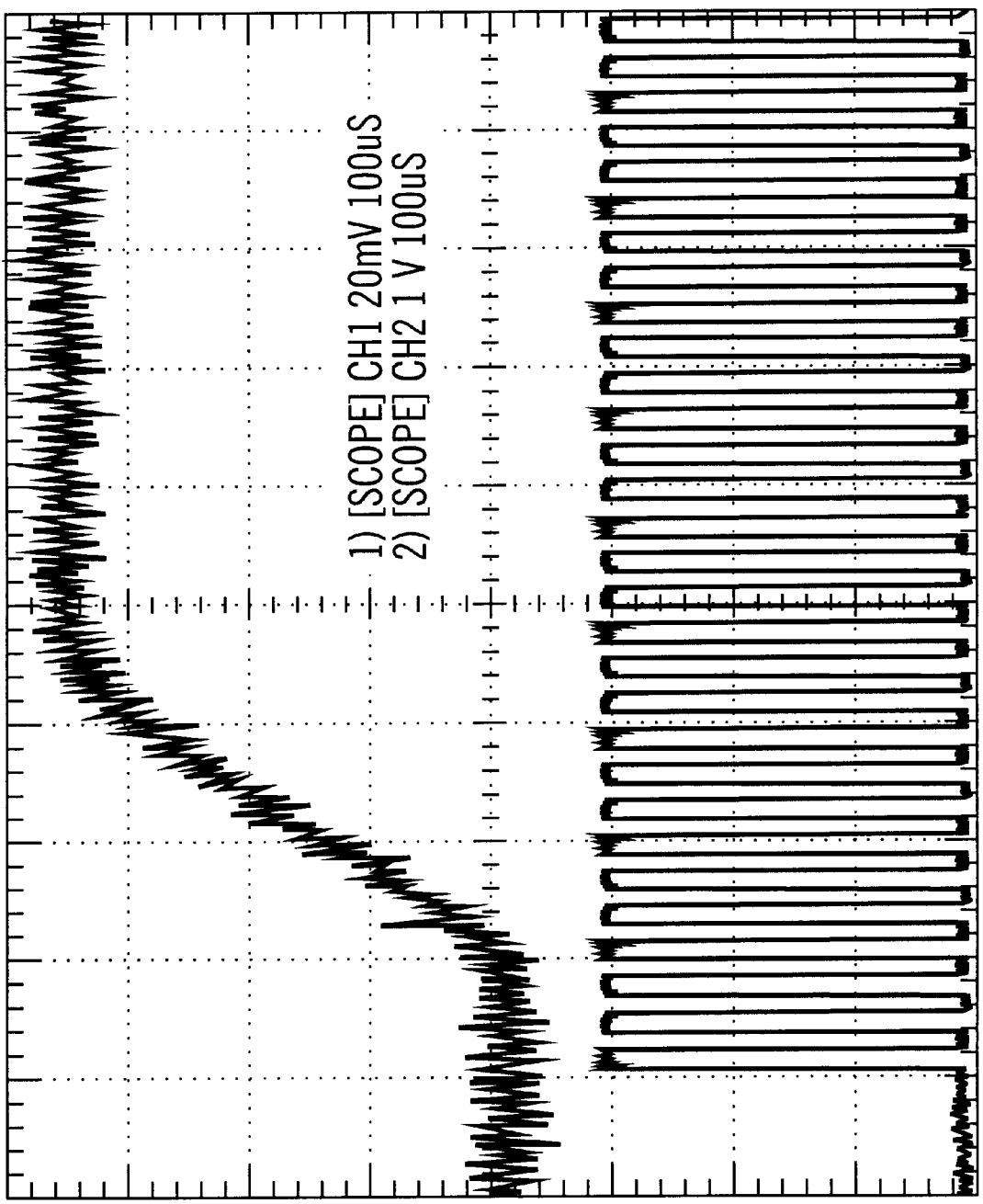
FIG. 10 is a waveform diagram illustrating operation of the safety circuit and power supplied to a DC motor that is an enlarged view of the portion shown in the dashed circle 10—10 of FIG. 9.
Figure 11:
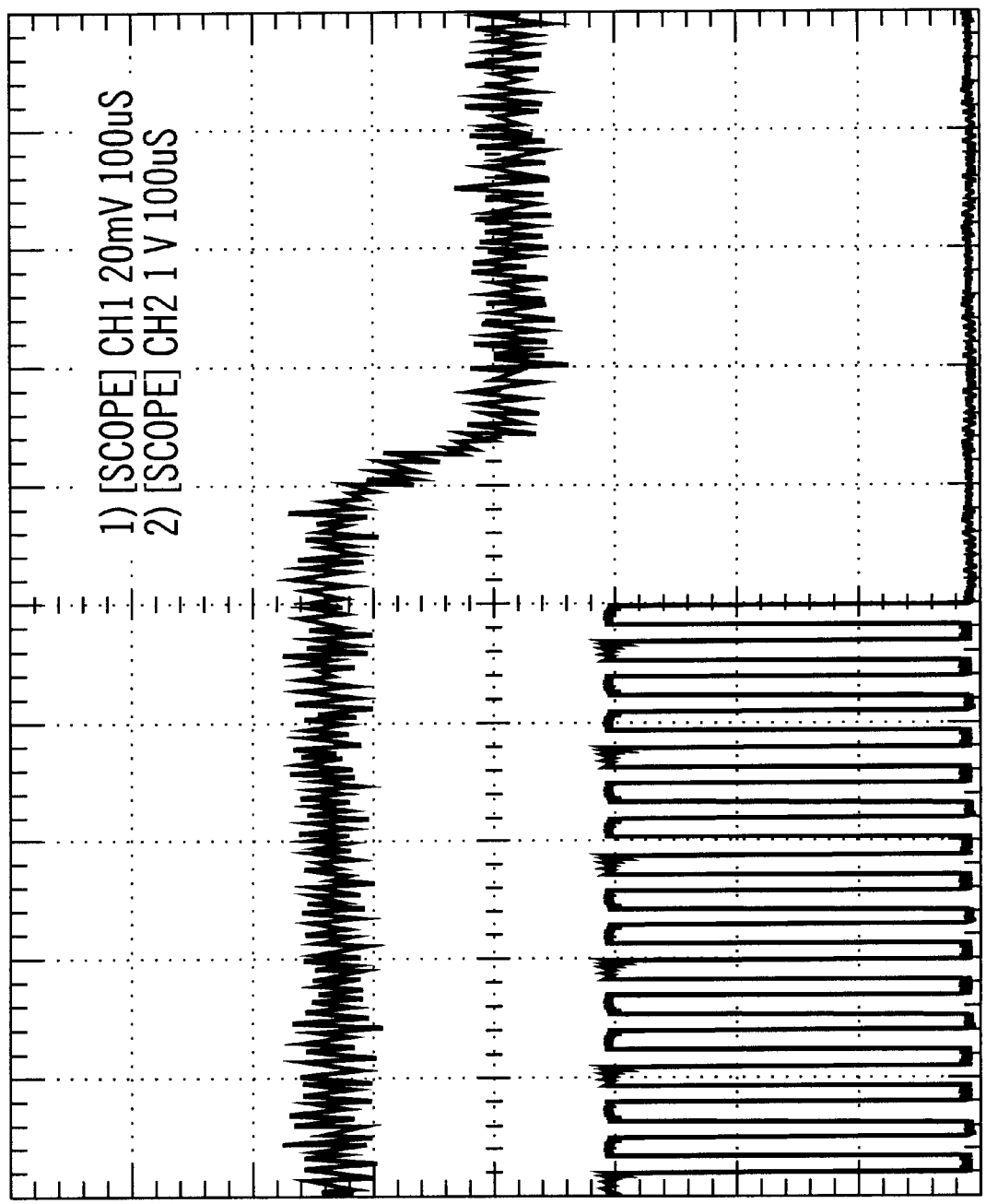
FIG. 11 is a waveform diagram illustrating operation of the safety circuit and power supplied to a DC motor that is an enlarged view of the portion shown in the dashed circle 11—11 of FIG. 9.

When an AC voltage potential signal (e.g., a 3 volt Peak to Peak square wave at a frequency of approximately 32 kHz—see FIGS. 9–11) is applied to terminal 3 of the safety circuit 300, Schottky diodes 304 and 306 rectify and double the signal to positively bias the gate G, current then flows from the drain D to the source S of the FET 308 and to terminal 1. This in turn drives the DC motor 302, which is connected to the positive DC voltage potential at terminal 2. In alternative embodiments, a different number of components, such as diodes, capacitors, resistors, or the like, may be used. In addition, the selection of the type of FET, diode, size of the voltage potentials on terminals 1, 2 and 3, the AC signal type (including duration of peaks, waveform and frequency), may be different, with the selection being dependent on motor nominal operating voltage, system friction, tolerances, safety issues, control electronics, or the like.

In preferred embodiments, the safety circuit 300 uses the additional AC signal to control the forward operation of the DC motor 302, since concerns over DC motor "run away" arise mainly from the possibility of over delivery of a fluid due to the failure of the safety circuit 300. There is less concern for the situation, in which the fluid delivery system rewinds, since no fluid would be delivered in that scenario. However, in alternative embodiments, the drive system may also use an additional signal to control operation of the DC motor in the rewind direction.

Figure 4:
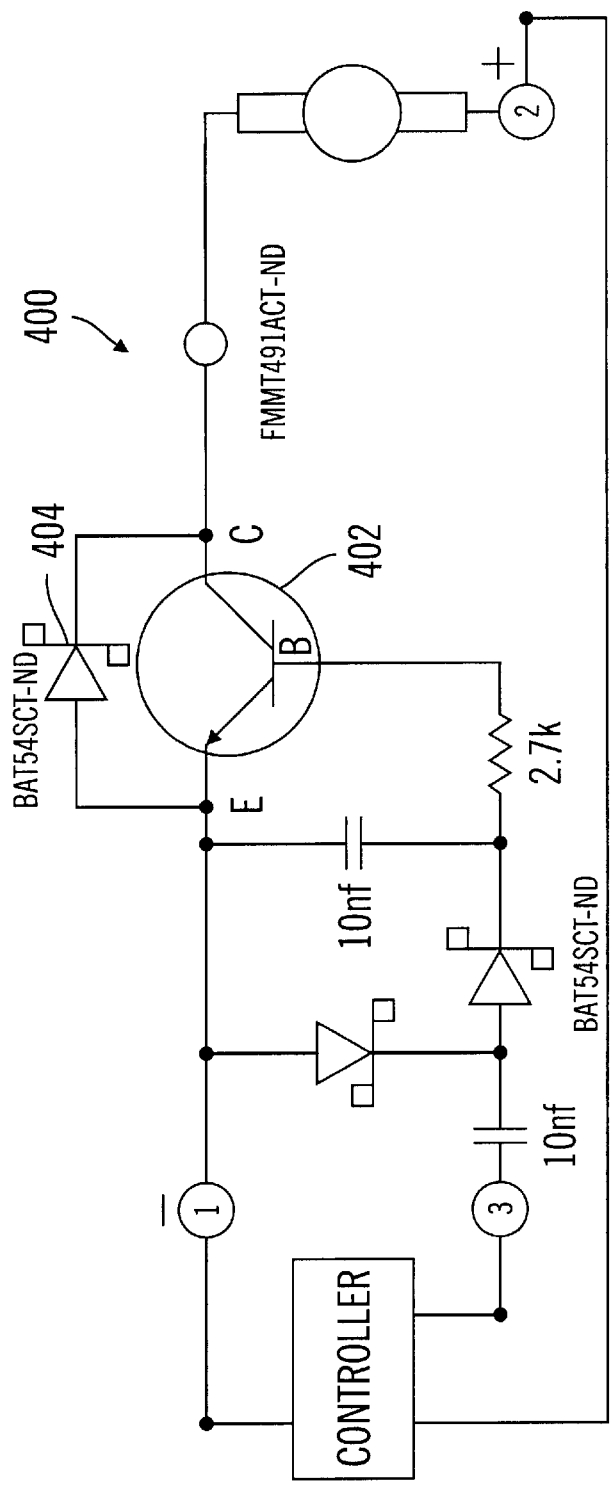
FIG. 4 is a schematic diagram of a safety circuit that is a variation of the embodiment shown in FIG. 3.

FIG. 4 illustrates a safety circuit 400 in accordance with a fourth embodiment of the present invention. This safety circuit 400 is similar to the embodiment of FIG. 3, but utilizes a BJT 402 (FMMT 491 ACT-ND from Zetex) instead of the FET 308, and an additional Schottky diode 404 (e.g., BAT54CT-ND from Zetex).

FIGS. 5(a)–(c) illustrate a safety circuit 500 in accordance with a fifth embodiment of the present invention. This safety circuit 500 is also similar to the embodiment of FIG. 3, but utilizes FET 502 (IRLM1902 from International Rectifier) instead of the FET 308, and an additional Schottky diode 504 (e.g., BAT54CT-ND from Zetex).

Figure 6:
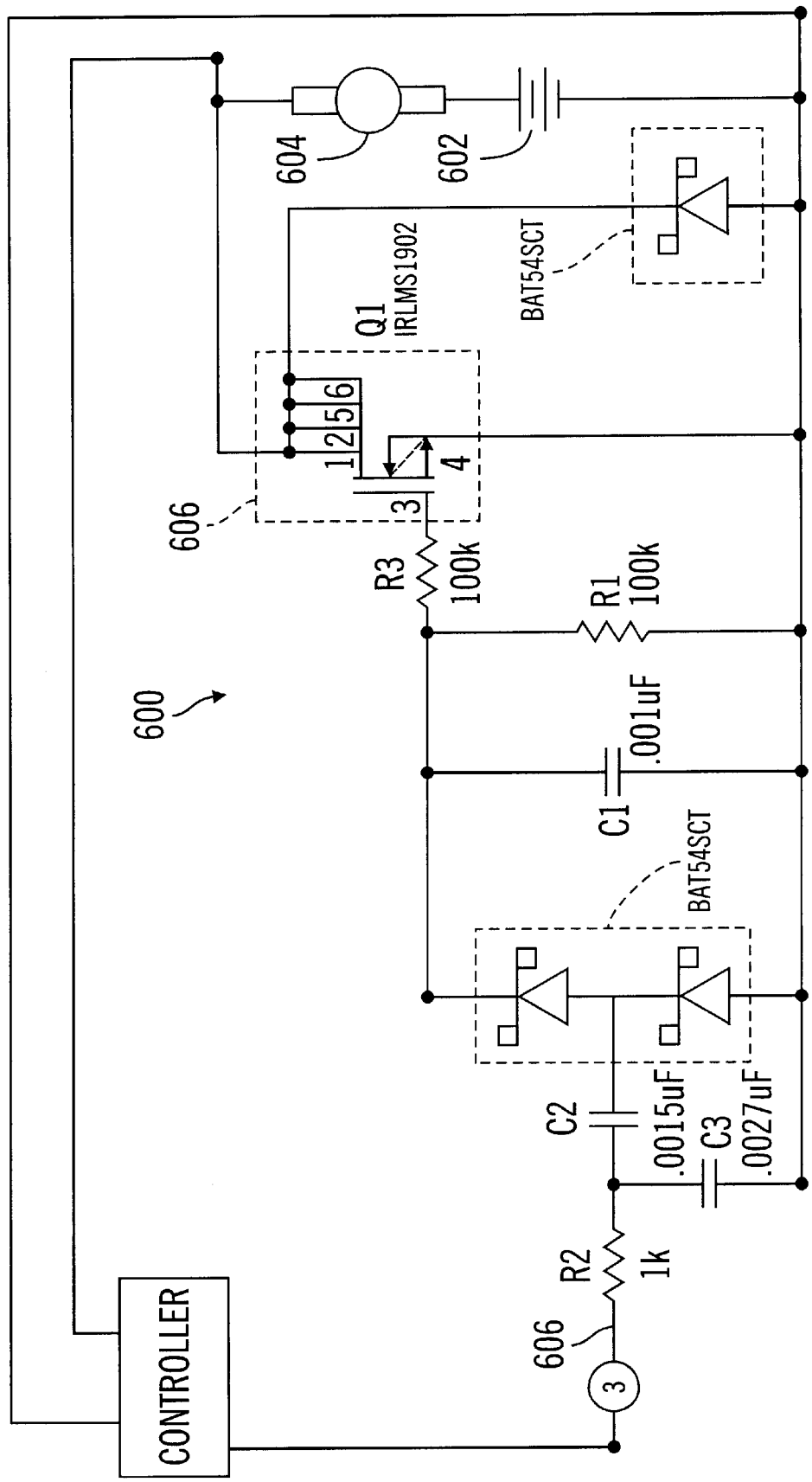
FIG. 6 is a schematic diagram of a safety circuit that is yet another variation of the embodiment shown in FIG. 3.

FIG. 6 illustrates a safety circuit 600 in accordance with a sixth embodiment of the present invention. This safety circuit 600 is similar to the embodiment of FIG. 3, but utilizes FET 606 (IRLM1902 from International Rectifier) instead of the FET 308, and an additional Schottky diode (e.g., BAT545CT-ND from Zetex). In addition, the capacitors and resistors are selected to form a bandpass filter to provide better noise isolation and circuit performance. Performance of the safety circuit 600 as it provides power to the DC motor 604 from a battery 602 is illustrated in FIGS. 9–11.

FIG. 7 illustrates a perspective view of a DC motor package 700 that includes a safety circuit 702 within the package 700 holding a DC motor 704. An advantage to this configuration arises from the fact that the DC motor 704 includes the safety circuit 702, which must be connected, and enabled, or the DC motor 704 will not operate. This minimizes the possibility that a DC motor 704 will be improperly installed in a fluid delivery device by assuring that an AC signal must be provided to the terminal input 3 on wire 706 to enable the DC motor 704 to operate. In alternative embodiments, as shown in FIG. 8, the fluid delivery system 800 includes an additional safety circuit 802 (i.e., in addition to other switches and controls found in the control circuitry), which is contained within the control electronics 804. The control electronics 804 are then connected to a standard, two-input DC motor 806, without the need for an additional connection to the DC motor 806. For instance, the safety circuit 802 operates a switch 808 to enable power to pass to and drive the DC motor 806.

FIGS. 9–11 illustrate operational waveforms for the safety circuit 600 (see FIG. 6) as DC current is applied to the circuit. As shown in FIG. 9, when DC current is applied to the DC motor 604 in graph section 902, no current is drawn since the AC enable signal in graph section 908 is not present. When the AC signal is applied in graph section 910, the DC current is quickly applied to the DC motor 604 by the battery 602, as shown by the graph section 904. When the AC enable signal is removed, as shown in graph section 912, the DC power supplied to the DC motor 604 is cutoff, as shown in graph section 906. FIGS. 10 and 11 highlight and expand portions of FIG. 9 to illustrate the AC signal used and the response of the safety circuit 600. The illustrated AC signal is at approximately 3 volts peak-to-peak at a frequency of approximately 32 kHz. However, in alternative embodiments, different shape waveforms, such as saw tooth, sinusoidal, or the like may be used. In addition, different voltage ranges may be used, with the selection being dependent on the rated motor output and the application in which the motor is being used. Further, higher or lower frequencies may be utilized, with the selection be dependent on the response characteristics of the safety circuit, noise, or the like. The delays observed in FIGS. 10 and 11 are a result of the smoothing and bandpass filters used in the safety circuit 600. For instance it takes approximately 125 microseconds for the DC motor 604 to respond after the AC signal is provided, and about 80 microseconds for the DC motor 604 to respond to termination of the AC signal. One advantage of having the DC current ramp up and down is that it minimizes the effects of voltage spikes and electromagnetic interference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A safety circuit system for a DC motor for use with a fluid delivery system, the safety circuit system comprising:
   a first voltage potential DC power line coupled to provide a first voltage potential to the DC motor;
   a second voltage potential DC power line coupled to provide a second voltage potential to the DC motor, wherein the second voltage potential is different from the first potential;
   a controller that controls at least the first voltage potential on the first voltage potential DC power line;
   a safety circuit having an enable state and a disable state, wherein a default state is the disable state, wherein the safety circuit is coupled to the controller, wherein the controller controls the safety circuit to place the safety circuit in the enable state independently of controlling the first voltage potential on the first voltage potential DC power line, and wherein the safety circuit is operatively coupled to at least one of the first and second voltage potential DC power lines to inhibit DC flow and forward motion of the DC motor when the safety circuit is in the disable state and to permit DC flow and forward motion of the DC motor when the safety circuit is in the enable state such that the forward motion of the DC motor will occur when the safety circuit is in the enable state.

2. The safety circuit system according to claim 1, wherein the safety circuit is controlled by an AC signal from the controller such that the safety circuit is enabled by an AC signal to permit DC to flow and enable the forward motion of the DC motor while the AC signal is provided by the controller.

3. The safety circuit system according to claim 1, wherein the safety circuit in the disable state operates to inhibit the forward motion of the DC motor when the difference of the second voltage potential from the first voltage potential is positive.

4. The safety circuit system according to claim 3, wherein the safety circuit in the disable state is inoperative to inhibit a reverse motion of the DC motor when the difference of the second voltage potential from the first voltage potential is negative.

5. The safety circuit system according to claim 3, wherein the safety circuit in the disable state operates to inhibit a reverse motion of the DC motor when the difference of the second voltage potential from the first voltage potential is negative.

6. The safety circuit system according to claim 1, wherein the safety circuit in the disable state operates to inhibit the forward motion of the DC motor when the difference of the second voltage potential from the first voltage potential is negative.

7. The safety circuit system according to claim 3, wherein the safety circuit in the disable state is inoperative to inhibit a reverse motion of the DC motor when the difference of the second voltage potential from the first voltage potential is positive.

8. The safety circuit system according to claim 3, wherein the safety circuit in the disable state operates to inhibit a reverse motion of the DC motor when the difference of the second voltage potential from the first voltage potential is positive.

9. The safety circuit system according to claim 1, wherein the fluid delivery device is an infusion pump, and wherein the safety circuit is used to prevent operation of the DC motor during a controller failure to prevent accidental delivery of excess fluid.

10. The safety circuit system according to claim 1, wherein the safety circuit is integral with the DC motor.

11. The safety circuit system according to claim 1, wherein the safety circuit is co-located with the controller.

12. A safety circuit system for a DC driven device for use with a fluid delivery system, the safety circuit system comprising:

a first voltage potential DC power line coupled to provide a first voltage potential to the DC driven device;

a second voltage potential DC power line coupled to provide a second voltage potential to the DC driven device, wherein the second voltage potential is different from the first potential;

a controller that controls at least the first voltage potential on the first voltage potential DC power line;

a safety circuit having an enable state and a disable state, wherein a default state is the disable state, wherein the safety circuit is coupled to the controller, wherein the controller controls the safety circuit to place the safety circuit in the enable state independently of controlling the first voltage potential on the first voltage potential DC power line, and wherein the safety circuit is operatively coupled to at least one of the first and second voltage potential DC power lines to inhibit DC flow and operation of the DC driven device when the safety circuit is in the disable state and to permit DC flow and operation of the DC driven device when the safety circuit is in the enable state such that the operation of the DC driven device will occur when the safety circuit is in the enable state.

13. The safety circuit system according to claim 12, wherein the DC driven device is a DC motor, and wherein the fluid delivery system is an infusion pump.

14. The safety circuit system according to claim 12, wherein the DC driven device is a gas generator, and wherein the fluid delivery system is an infusion pump.

15. The safety circuit system according to claim 12, wherein the safety circuit is controlled by an AC signal from the controller such that the safety circuit is enabled by an AC signal to permit DC flow and enable the forward motion of the DC motor while the AC signal is provided by the controller.

* * * * *